United States Patent
Wheat et al.

(10) Patent No.: US 10,422,776 B2
(45) Date of Patent: Sep. 24, 2019

(54) METHODS FOR PREPARING LIQUID MIXTURES

(71) Applicant: Waters Technologies Corporation, Milford, MA (US)

(72) Inventors: Thomas E. Wheat, Hopedale, MA (US); Patricia McConville, Cumberland, RI (US); John R. Lamoureux, Franklin, MA (US); Aparna Chavali, Chapel Hill, NC (US)

(73) Assignee: Waters Technologies Corporation, Milford, MA (US)

( * ) Notice: Subject to any disclaimer, the term of this patent is extended or adjusted under 35 U.S.C. 154(b) by 157 days.

(21) Appl. No.: 15/309,725

(22) PCT Filed: May 8, 2015

(86) PCT No.: PCT/US2015/029870
§ 371 (c)(1),
(2) Date: Nov. 8, 2016

(87) PCT Pub. No.: WO2015/172011
PCT Pub. Date: Nov. 12, 2015

(65) Prior Publication Data
US 2017/0269041 A1  Sep. 21, 2017

Related U.S. Application Data

(60) Provisional application No. 61/990,888, filed on May 9, 2014.

(51) Int. Cl.
*G01N 30/34* (2006.01)
*G01N 30/86* (2006.01)
(Continued)

(52) U.S. Cl.
CPC ........... *G01N 30/34* (2013.01); *B01D 15/168* (2013.01); *G01N 30/8658* (2013.01); *G01N 2030/027* (2013.01); *G01N 2030/347* (2013.01)

(58) Field of Classification Search
CPC ........... B01D 15/168; G01N 2030/027; G01N 2030/347; G01N 30/34; G01N 30/8658; G01N 2030/342; G01N 30/02; G01N 2030/324; G01N 2030/326; G01N 2030/8813; G01N 2030/8831;
(Continued)

(56) References Cited

U.S. PATENT DOCUMENTS

| | | | | |
|---|---|---|---|---|
| 6,106,721 A * | 8/2000 | Bouvier | ............... | B01D 15/00 210/198.2 |
| 6,221,250 B1 * | 4/2001 | Stafstrom | .............. | G01N 30/34 210/101 |

(Continued)

*Primary Examiner* — Randy W Gibson
*Assistant Examiner* — Gedeon M Kidanu

(57) ABSTRACT

A method of preparing a liquid mixture for use in a liquid chromatography system is provided. The mixture comprises one or more acids, one or more bases, one or more solvents and water, and the method comprises the steps of: calculating pH and/or solvent concentration at a particular time t from a user-determined gradient function; and, based on the values obtained, calculating percent acid, percent base, percent solvent and percent water in the liquid mixture at time t. A liquid chromatography system incorporating such method is also provided.

20 Claims, 4 Drawing Sheets

(51) Int. Cl.
*B01D 15/16* (2006.01)
*G01N 30/02* (2006.01)

(58) Field of Classification Search
CPC .. G01N 2030/884; G01N 30/24; G01N 30/36; G01N 30/482; G01N 30/8672
See application file for complete search history.

(56) References Cited

U.S. PATENT DOCUMENTS

| | | | |
|---|---|---|---|
| 6,299,767 B1* | 10/2001 | Dourdeville | B01D 15/166 210/101 |
| 2002/0009388 A1* | 1/2002 | Lombardo | G01N 30/8682 436/161 |
| 2002/0117447 A1* | 8/2002 | Wheat | B01D 15/166 210/656 |
| 2005/0182257 A1* | 8/2005 | Antonini | B01D 15/20 546/44 |
| 2005/0247625 A1* | 11/2005 | Liu | B01D 15/166 210/635 |
| 2008/0053830 A1* | 3/2008 | Tsonev | B03C 5/00 204/661 |
| 2008/0279038 A1* | 11/2008 | Bellafiore | G05D 11/139 366/152.4 |
| 2013/0206666 A1* | 8/2013 | Andrews | G01N 30/34 210/198.2 |
| 2016/0069844 A1* | 3/2016 | Jackson | G01N 30/06 73/61.55 |

* cited by examiner

METHODS FOR PREPARING LIQUID MIXTURES

RELATED APPLICATIONS

This application is the National Stage of International Application No. PCT/US2015/029870, filed on May 8, 2015, which claims priority to and benefit of U.S. Provisional Patent Application No. 61/990,888, entitled "Methods for Preparing Liquid Mixtures," filed May 9, 2014. This application is related to U.S. application Ser. No. 13/695,811 filed Apr. 29, 2010, which is the National Stage of International Application No. PCT/US11/37645 filed May 24, 2011, which claims priority to and benefit of U.S. Provisional Patent Application No. 61/348,280, filed May 26, 2010. The entire contents and teachings of each of these applications are hereby expressly incorporated herein by reference in their entirety.

FIELD OF THE INVENTION

The present invention relates to liquid mixtures. More specifically, the invention pertains to methods of preparing liquid mixtures of known pH and solvent concentration for use in various methods in analytical chemistry, such as liquid chromatography systems.

BACKGROUND OF THE INVENTION

Liquid chromatography is a form of chromatography used frequently in biochemistry and analytical chemistry to separate, identify, and quantify compounds based on their properties such as polarity and their interactions with a stationary phase. Liquid chromatography can be performed using planar or column techniques. In both cases, the system includes a chromatographic device with a stationary phase, a means for moving a mobile phase (solvent carrying compounds of interest) through the device (such as a pump, or gravity), and a detector that creates a signal to identify a particular compound based on the time of the signal and the amount of the compound based on the intensity of the signal. The detector may also provide other characteristic information (e.g. UV/Vis spectroscopic data for a compound if so equipped). The detector may also be a mass spectrometer. Retention time of a compound in the device varies depending on the strength of the compound's interactions with the stationary and mobile phases, the ratio/composition of the mobile phase that is used, and the flow rate of the mobile phase.

The composition of the mobile phase flowing through the chromatographic device is critical to obtaining the required separation of compounds. For example, in reversed-phase chromatography, it can be useful to adjust the pH of the mobile phase to control the selectivity and resolution of the chromatographic separation. Small increments of pH change can have significant impact on the effectiveness and suitability of the chromatographic separation. However, manual preparation of the numerous acid and base buffer solutions for such analyses is time consuming and error-prone. Prior art systems have allowed users to blend multiple solvents to create mobile phases of particular pH. However, in these systems the user was required to know not only the pH of their particular solvents, but also the pH that would result from mixing the solvents in various proportions. It would be desirable to have a system and method for automatically calculating and blending buffer solutions and the organic and aqueous mobile phase componentsto produce a particular pHspecified by a user, and for varying the proportions of buffer and solvents over the course of the elution. It would also be desirable to have buffer solutions and mobile phase combinations that are compatible with reversed-phase mass spectrometry over a large pH range.

SUMMARY OF THE INVENTION

Accordingly, in one aspect the invention provides a method of preparing a liquid mixture, the mixture comprising one or more acids, one or more bases, and one or more solvents, the method comprising the steps of : i) calculating pH and/or solvent concentration at a particular time t from a user-determined gradient function; and ii) based on the values obtained in step (i), calculating percent acid, percent base, and percent solvent in the liquid mixture at time t.

In additional aspects, the invention also provides a computer program for determining relative proportions in a liquid mixture according to the above algorithm, wherein the proportions are used for controlling a liquid mixture preparation device. Also provided is an eluent preparation device comprising i) a liquid mixture preparation device comprising a mixed liquid outlet port and a plurality of inlet ports connected to component sources of at least one of an acid, a base, a solvent, and water and ii) a mixer control unit arranged to control the relative component proportions supplied through the inlet ports of the liquid mixture preparation device, wherein the mixer control unit i) calculates pH and/or solvent concentration at a particular time t from a user-determined gradient function; and ii) based on the values obtained in step (i), calculates percent acid, percent base, and percent solvent in the liquid mixture at time t.

A liquid chromatography system comprising an eluent preparation device is also provided.

DESCRIPTION OF THE DRAWINGS

The invention is further illustrated by the following drawings in which.

DETAILED DESCRIPTION OF THE INVENTION

Figure 1:
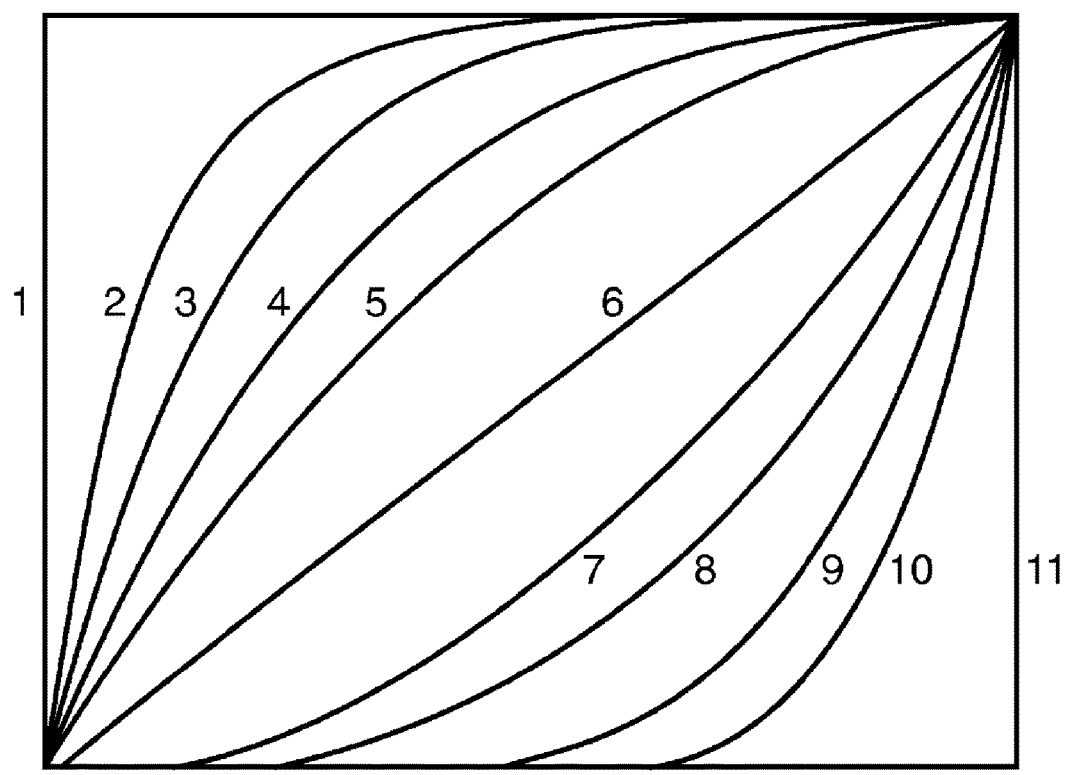
FIG. 1 is a diagram of different curves that can be used to change the pH and organic solvent concentration over the course of an elution.
Figure 2:
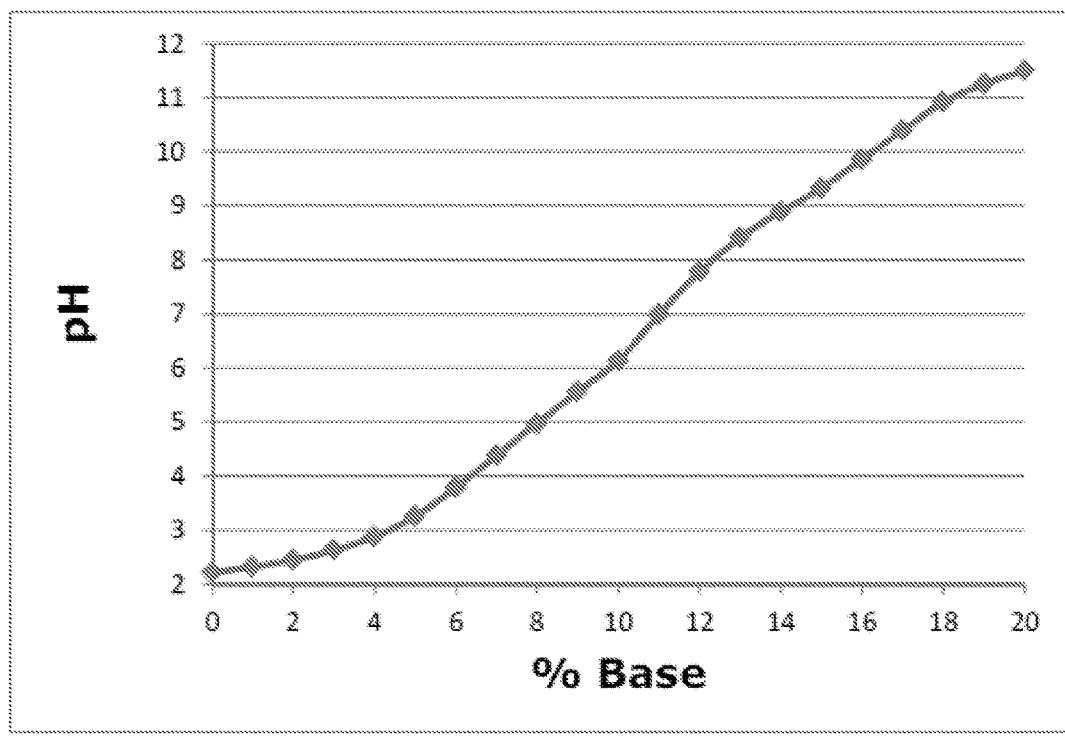
FIG. 2 illustrates an exemplary relationship between mobile phase pH and proportion of base buffer component.

As used herein in the specification and claims, including as used in the examples and unless otherwise expressly specified, all numbers may be read as if prefaced by the word "about", even if the term does not expressly appear. Also, any numerical range recited herein is intended to include all sub-ranges subsumed therein.

The chromatographic system uses four stock solvents to create the desired pH-solvent gradients for an elution, the solvents comprising an acid solution, a base solution, a solvent, and water. In exemplary embodiments, the acid and base buffer solutions include volatile acids and bases that are compatible with mass spectrometry, e.g., electrospray ionization mass spectrometry. The acid and base solutions can include a combination of various components. For example, the acid solution can include maleic acid, citric acid and succinic acid. The base solution can include, for example, 4-methyl morpholine, morpholine, ammonium hydroxide and piperidine. The solvent can be any organic solvent compatible with reversed-phase LC/MS, e.g., acetone, acetonitrile, methanol, ethanol, n-propanol and isopropanol, tetrahydrofuran (THF) or any other compatible organic solvent. The water component can be distilled and/or deionized water.

These four stock solutions are metered in different relative concentrations to generate a given pH condition for the delivered mobile phase at a given point of time.

In an embodiment of the invention, four different types of data can be entered by the user into the computer program which controls operation of the chromatography system and specifically delivery of the correct solutions at the pump: 1) a pH-gradient table; 2) an empirical pH calibration table (or $pK_a$); 3) molar concentrations of acid and base stock solutions; and 4) the desired acid+base molar concentration that will be delivered to the stationary phase.

A pH look-up table is used by the software to calculate the percentage flow from acid solution and base solution lines during the elution. The look-up table is created by the software either from a user-input $pK_a$ or from a user-input empirical calibration table. The empirical calibration table is created by the user by mixing the 2-4 solutions in known proportions and measuring the pH. The software then uses these input values to calculate the percent acid and base (described further below) at a given time point in the gradient table.

The gradient that is delivered to the stationary phase is determined in the following manner, based on the user-entered information.

A pH-solvent gradient table includes values for 1) flow rate, 2) pH, and 3) change in pH, (referred to herein as a "pH curve"). In some embodiments, the a pH gradient table can also include values for 4) organic solvent concentration and 5) change in organic solvent concentration (referred to herein as the "solvent gradient curve"), for each time t during the course of the separation. The pH-solvent gradient table can have any number of rows for any range of times. Typically, a user will prepare a table having 5 to 6 rows, for times $t_0$ to $t_5$ (or $t_6$). An example of a pH-solvent gradient table is shown in Table 1:

TABLE 1

| Time (min) | Flow (mL/min) | pH | pH Curve | % Organic | Solvent Gradient Curve |
|---|---|---|---|---|---|
| Init. | 0.5 | 6.8 | ... | 0 | ... |
| 10 | 0.5 | 6.8 | 6 | 40 | 6 |
| 12 | 0.5 | 6.8 | 6 | 60 | 6 |
| 15 | 0.5 | 6.8 | 11 | 80 | 11 |

Each time period, for example the time from $t_1$ to $t_2$, is referred to a "time segment". The pH or solvent gradient curve determines how the pH or organic solvent concentration will change over that particular time segment. Examples of curves, which can be used to vary both the pH and organic solvent concentration are depicted in the FIG. 1. The change can be linear, where halfway through the time segment the percentages are halfway between the starting and the ending percentages. The change may also occur more quickly at the beginning of the time segment and more slowly at the end of the segment, a convex curve. The opposite pattern, a concave curve is also possible. The change can also be a step at either the beginning or the end of the segment. The change of pH and organic solvent concentration can be independently varied or held constant from one time segment to another, depending on the needs of the user.

The pH-solvent gradient table is prepared by the user based on experimentation and prior experience with particular solvents and analytes of interest, and is within the ability of one skilled in the art of chromatography systems.

The user enters the $pK_a$ from which the look-up table is calculated, or they may enter an empirical calibration from which the pH look-ups are calculated, into the computer program. Optionally, the system can include pre-generated look-up tables for common buffer systems that can be selected by the user. The look-up table can be a one-variable, two-variable or three-variable table; in each, the pH is calculated or measured based on the values of the other variables. A three-variable table will have values for temperature, organic solvent concentration and base percent (%); a two-variable look-up table will have values for solvent concentration (molar) and base percent (%), and a one-variable look-up table has values for base percent. The one-variable table can either be directly entered by the user or calculated by the software based on an input value for the $pK_a$ of the acid used. Typically, a two-variable look-up table may have between 30-60 rows, and a one-variable look-up table will have fewer rows. The two- and three-variable look-up tables are constructed by manually preparing specific mixtures of acid and base buffers, organic solvent and water, and for the three-variable table, temperature. The pH of each mixture at the given conditions is measured and entered into the table.

The user also enters the molar concentrations for each of the acid and base stock solutions that will be combined at the pump in the system. The user can also enter the percentages of solvent and water that will be combined at the pump in the system.

A final component of the user-entered information is the delivered acid+base concentration. It has been found from experience that a convenient ratio of acid+base percent and solvent percent is about 20% acid+base, and about 80% solvent. However, these numbers are not required, and can be adjusted according to the needs of the user and the analytes being separated.

At a point in time, the pump in the chromatography systems is delivering the specified total flow rate of liquid to the separation column. The software calculates the pH and solvent concentration at a particular time t, using the information provided in the gradient table and the look-up table, and a fraction multiplier calculated using the particular pH curve and/or solvent curve in the gradient table. Then, for this particular pH and salt concentration, the % base, % acid, and % solvent can be calculated, using interpolation, from values provided in the pH look-up table. These values are sent to the chromatographic system to generate the specific mobile phase conditions for time t.

The method of the invention is further illustrated by way of the following example.

TABLE 2 pH-Solvent Gradient Table (provided by the user)

| time (min) | flow (ml/min) | pH | pH curve | % Organic | Solvent Gradient Curve |
|---|---|---|---|---|---|
| $T_0 = 0$ | 1.0 ($f_0$) | 5 ($pH_0$) | — | 0 | — |
| $T_1 = 10$ | 1.0 ($f_1$) | 6 ($pH_1$) | 6 ($pHC_1$) | 20 | 6 ($sCC_1$) |
| $T_2 = 15$ | 1.0 ($f_2$) | 5 ($pH_2$) | 6 ($pHC_2$) | 40 | 6 ($sCC_2$) |
| $T_3 = 16$ | 0 ($f_3$) | 5 | 11 | 60 | 11 |

TABLE 3.1

One Variable - pH Look-Up Table
(empirical calibration table)

| base % | pH |
|---|---|
| 0 | 4.0 |
| 5 ($bP_0$) | 5.0 ($pHL_0$) |
| 10 ($bP_1$) | 5.5 ($pHL_1$) |
| 20 | 6.0 |

TABLE 3.2

Two Variables - pH Look-Up Table
(empirical calibration table)

| % Organic Solvent | Base % | pH |
|---|---|---|
| 20 ($sPL_0$) | 5 ($bP_0$) | 5.0 ($pHL_0$) |
| 20 ($sPL_0$) | 10 ($bP_1$) | 5.5 ($pHL_1$) |
| 40 ($sPL_1$) | 5 ($bP_0$) | 5.2 ($pHL_2$) |
| 40 ($sPL_1$) | 10 ($bP_1$) | 5.7 ($pHL_3$) |
| ... | ... | ... |

TABLE 3.3

Three Variables - pH Look-Up Table
(empirical calibration table)

| Temp. ° C. | % Organic Solvent | Base % | pH |
|---|---|---|---|
| 20° C. ($Temp_0$) | 20 ($sPL_0$) | 5 ($bP_0$) | 5.0 ($pHL_0$) |
| 20° C. ($Temp_0$) | 20 ($sPL_0$) | 10 ($bP_1$) | 5.5 ($pHL_1$) |
| 20° C. ($Temp_0$) | 40 ($sPL_1$) | 5 ($bP_0$) | 5.2 ($pHL_2$) |
| 20° C. ($Temp_0$) | 40 ($sPL_1$) | 10 ($bP_1$) | 5.7 ($pHL_3$) |
| 30° C. ($Temp_1$) | 20 ($sPL_0$) | 5 ($bP_0$) | 5.05 ($pHL_4$) |
| 30° C. ($Temp_1$) | 20 ($sPL_0$) | 10 ($bP_1$) | 5.56 ($pHL_5$) |
| 30° C. ($Temp_1$) | 40 ($sPL_1$) | 5 ($bP_0$) | 5.24 ($pHL_6$) |
| 30° C. ($Temp_1$) | 40 ($sPL_1$) | 10 ($bP_1$) | 5.77 ($pHL_7$) |

Molar Concentrations (Provided by the User):
  acid concentration: acU=100 mM
  base concentration: bcU=100 mM
  organic solvent concentration: scU=1000 mM
  acid and base concentration (bufferConcentrationU)=20 mM
  (bufferConcentrationU≤min (acU, bcU)
Gradient Function The gradient function is defined by the following set of equations:

$$y = y_s + (y_n - y_s) \times \text{fraction} \quad \text{equation 1}$$

where y is pH and salt concentration (or solvent, if an organic solvent is used), and "fraction" is defined as follows (where values for $t_1$ and $t_0$ are obtained from the pH—salt gradient table, and t is the time of interest, $t_0 \leq t \leq t_1$):

Curve 1:
$$\text{fraction} = 1.0 \quad \text{equation 2}$$

Curve 2:
$$\text{fraction} = 1 - \left(1 - \frac{t}{t_1 - t_0}\right)^8$$

Curve 3:
$$\text{fraction} = 1 - \left(1 - \frac{t}{t_1 - t_0}\right)^5$$

Curve 4:
$$\text{fraction} = 1 - \left(1 - \frac{t}{t_1 - t_0}\right)^3$$

Curve 5:
$$\text{fraction} = 1 - \left(1 - \frac{t}{t_1 - t_0}\right)^2$$

Curve 6:
$$\text{fraction} = \frac{t}{t_1 - t_0}$$

Curve 7:
$$\text{fraction} = \left(\frac{t}{t_1 - t_0}\right)^2$$

Curve 8:
$$\text{fraction} = \left(\frac{t}{t_1 - t_0}\right)^3$$

Curve 9:
$$\text{fraction} = \left(\frac{t}{t_1 - t_0}\right)^5$$

Curve 10:
$$\text{fraction} = \left(\frac{t}{t_1 - t_0}\right)^8$$

Curve 11:
fraction = 0 if $t < (t_1 - t_0)$ and
fraction = 1 if $t = (t_1 - t_0)$.

pH and Solvent Concentration at Any Gradient Time t

At any gradient time t, the pH value can be calculated from the gradient function, Equation 1 above, as follows:
From Table 2, the pH—Solvent Gradient Table, y=pH, $y_s = pH_0$, and $y_n = pH_1$, for all values of t where $t_0 \leq t \leq t_1$.
Using curve 6 as an example, the fraction is $$\frac{t}{t_1 - t_0}.$$

At time t, $$pH(t) = pH_0 + (pH_1 - pH_0) \times \frac{t}{t_1 - t_0}. \quad \text{equation 3}$$

Similarly, at time t, and using curve 6 as an example, the salt concentration is calculated as:

$$sC(t) = sC_0 + (sC_1 - sC_0) \times \frac{t}{t_1 - t_0}.$$ equation 4

Calculation of Base Percent 1) Using the one-variable pH Look-up table (Table 3.1), the base percent can be calculated, using interpolation, as follows:

$$BasePercent = bP_0 + \frac{bP_1 - bP_0}{pHL_1 - pHL_0} \times (pH - pHL_0)$$ equation 5.1

2) For a given organic solvent percent (sP) and pH, where $sPL_0 \le sP \le sPL_1$, $pHL_0 \le pH \le pHL_1$, and $pHL_2 \le pH \le pHL_3$, the base percent (%) can be calculated from the values provided by the user in the two-variable pH Look-up table (Table 3.2), using interpolation:

$$bPI_0 = bP_0 + \frac{bP_1 - bP_0}{pHL_1 - pHL_0} \times (pH - pHL_0)$$ equation 5.2

$$bPI_1 = bP_0 + \frac{bP_1 - bP_0}{pHL_3 - pHL_2} \times (pH - pHL_2)$$

then $$basePercent = bPI_0 + \frac{bPI_1 - bPI_0}{sPL_1 - sPL_0} \times (sP - sPL_0)$$

3) For a given temperature (Temp), solvent percent (sP) and pH, where $Temp_0 \le Temp \le Temp_1$, $sPL_0 \le sP \le sPL_1$, $pHL_0 \le pH \le pHL_1$, $pHL_2 \le pH \le pHL_3$, $pHL_4 \le pH \le pHL_5$, $pHL_6 \le pH \le pHL_7$, the base percent (%) can be calculated from the values provided by the user in the three-variable pH Look-up table (Table 3.3), using interpolation:

$$bPI_0 = bP_0 + \frac{bP_1 - bP_0}{pHL_1 - pHL_0} \times (pH - pHL_0)$$ equation 5.3

$$bPI_1 = bP_0 + \frac{bP_1 - bP_0}{pHL_3 - pHL_2} \times (pH - pHL_2)$$

$$bPI_2 = bP_0 + \frac{bP_1 - bP_0}{pHL_5 - pHL_4} \times (pH - pHL_4)$$

$$bPI_3 = bP_0 + \frac{bP_1 - bP_0}{pHL_7 - pHL_6} \times (pH - pHL_6)$$

$$bPI_4 = bPI_0 + \frac{bPI_1 - bPI_0}{sPL_1 - sPL_0} \times (sP - sPL_0)$$

$$bPI_5 = bPI_2 + \frac{bPI_3 - bPI_2}{sPL_1 - sPL_0} \times (sP - sPL_0)$$

and $$basePercent = bPI_4 + \frac{bPI_5 - bPI_4}{Temp_1 - Temp_0} \times (Temp - Temp_0)$$

Calculation of % A, % B, % C and % D in the Total Mixture (Sent to Gradient Proportioning Valve by Software)
1) Calculation of Solvent Percent Max $$acidPercent \times aCU + basePercent \times bCU = 100\% \times bufferConcentrationU$$ eq. 5.4.1

$$acidPercent + basePercent + solventPercent + aqueousPercent = 100\%$$ eq. 5.4.2

From equations 5.4.1 and 5.4.2 the following can be derived:

$$acidPercentMax = 100\% \times \frac{bufferConcentrationU}{aCU}$$ eq. 5.4.3

$$basePercentMax = 100\% \times \frac{bufferConcentrationU}{bCU}$$ eq. 5.4.4 and $$solventPercentMax =$$ eq. 5.4.5
$$100\% - (\text{max of } acidPercentMax \text{ and } basePercentMax)$$

2) Calculation Of Solvent Percentages Sent To Pump:
From equations 5.1, 5.2 or 5.3 basePercent is obtained. From this value, the following can be calculated:

$$acidPercent =$$ eq. 6.1
$$\frac{100\% \times bufferConcentrationU - basePercent \times bCU}{aCU}$$

From Equation 4, solventPercent is calculated as:

$$solventPercent = \frac{sC}{sCU} \times 100\%$$ eq. 6.2 if (solventPercent>solventPercentMax) then solventPercent=solventPercentMax $$aqueousPercent = 100\% - acidPercent - basePercent - solventPercent$$ eq. 6.3

The values for acidPercent, basePercent, solventPercent and aqueousPercent can be assigned to solvent A, B, C and D in the pumps.

Calculations for a One-Variable Look-Up Table from $pK_a$
For a given $pK_a$ value $pH_{min} = pK_a - 1$ $pH_{max} = pK_a + 1$ numPH=40 for arrayIndex=0 to arrayIndex=39, $$pH[arrayIndex] = pH_{min} + (pH_{max} - pH_{min}) \times \frac{arrayIndex}{numPH - 1}$$ equation 8

$$basePercent[arrayIndex] = \frac{10^{-pK_a}}{10^{-pK_a} + 10^{-pH[arrayIndex]}} \times 100\%$$ equation 9

So, for example, for a $pK_a=6.8$, $pH_{min}=5.8$, $pH_{max}=6.5$ and numPH=40,
a one-variable pH look-up table can be obtained from equations 8 and 9:

TABLE 4

| one-variable pH look-up | |
|---|---|
| Base % | pH |
| 9.09% | 5.8 |
| ... | ... |
| 50% | 6.8 |
| ... | ... |
| 90.9% | 7.8 |

The acid and base components can theoretically be any acid and base. In exemplary embodiments, the acid and base components each include combinations or mixtures of components to provide a combined mobile phase that is compatible with mass spectrometry, e.g., electrospray ionization mass spectrometry. For example, the acid solution can include maleic acid, citric acid and succinic acid. The base solution can include, for example, 4-methyl morpholine, morpholine, ammonium hydroxide and piperidine. Any suitable molar concentrations of the acid and base solution components can be selected. An exemplary acid solution can include or consist of 50 mM Maleic Acid, 25 mM Citric Acid, and 25 mM Succinic Acid. A corresponding exemplary base solution can include or consist of 50 mM 4-methyl Morpholine, 50 mM Morpholine, 50 mM Ammonium Hydroxide+50 mM Piperidine.

The solvent component can be any polar organic solvent compatible with reversed-phase LC/MS, e.g., acetone, acetonitrile, methanol, ethanol, n-propanol and isopropanol, tetrahydrofuran (THF) or any other compatible organic solvent.

Table 4 below illustrates an exemplary relationship between mobile phase pH and proportion of buffer solutions. Standard mixtures of the acid and base components were pipette and the pH was measured with a meter. Each sample was 80% water. The composition is expressed as % B (percent base) where % A (percent acid) is 20%-% B. The empirical table derived from these 21 points can be used by the data program to calculate the percentages of acid and base components required to deliver the programmed pH. As shown in Table 4, a broad pH range can be provided by mixtures of the acid and base components disclosed herein.

TABLE 4

| % B | pH |
|---|---|
| 0 | 2.22 |
| 1 | 2.32 |
| 2 | 2.45 |
| 3 | 2.63 |
| 4 | 2.88 |
| 5 | 3.26 |
| 6 | 3.79 |
| 7 | 4.38 |
| 8 | 4.97 |
| 9 | 5.57 |
| 10 | 6.14 |
| 11 | 6.99 |
| 12 | 7.78 |
| 13 | 8.41 |
| 14 | 8.89 |
| 15 | 9.32 |
| 16 | 9.85 |
| 17 | 10.4 |
| 18 | 10.9 |
| 19 | 11.3 |
| 20 | 11.5 |

In a preferred embodiment, e.g. in a liquid chromatographic system, the calculations are carried out by a data program, implemented from the equations given herein above, governing directly a metering device, such as a pump and valve system, or any other equivalent means of delivering the components to the chromatography device. The program preferably includes the ability to correct for separations carried out at different temperatures, by including temperature in the empirically-derived look-up table (as in Table 3.3). As will be understood by one skilled in the art, the invention is not limited to any particular flow rate, any particular mixing system, or any particular method of generating a flow through a chromatographic device. For example, the method of the invention can be used in both low pressure liquid chromatography (where mixing occurs prior to pumping), and high pressure liquid chromatography, where pumping occurs prior to mixing.

EXAMPLE

Analysis of Metoclopramide Mixture
  Instrument:
   ACQUITY UPLC H-Class System
   ACQUITY UPLC Photodiode Array Detector
   ACQUITY UPLC QDa Mass Detector
   ACQUITY Isocratic Solvent Manager with Restrictor
   Empower 3 Software
   Column: CSH C18, 2.1—50 mm
  Mobile Phase:
   Acid: 50 mM Maleic Acid; 25 mM Citric Acid; 25 mM Succinic Acid
   Base: 50 mM 4-methyl Morpholine; 50 mM Morpholine; 50 mM Ammonium Hydroxide;
   50 mM Piperidine
   Water
   Methanol
  Conditions:
   Gradient from 0-60% Methanol over 5 min at 0.6 mL/min at 40° C. Separations conducted at different pH conditions as discussed below.
  Samples:
   MS Start-Up Solution, (Waters P/N 700002741)
   Metoclopramide and impurities 0.06 mg/mL of the API and each of the 8 impurities
   (Impurity A, B, C, D, F, G, H and 9)

The described invention was used to provide different separation buffers to adjust resolution in the separation.

Figure 3A:
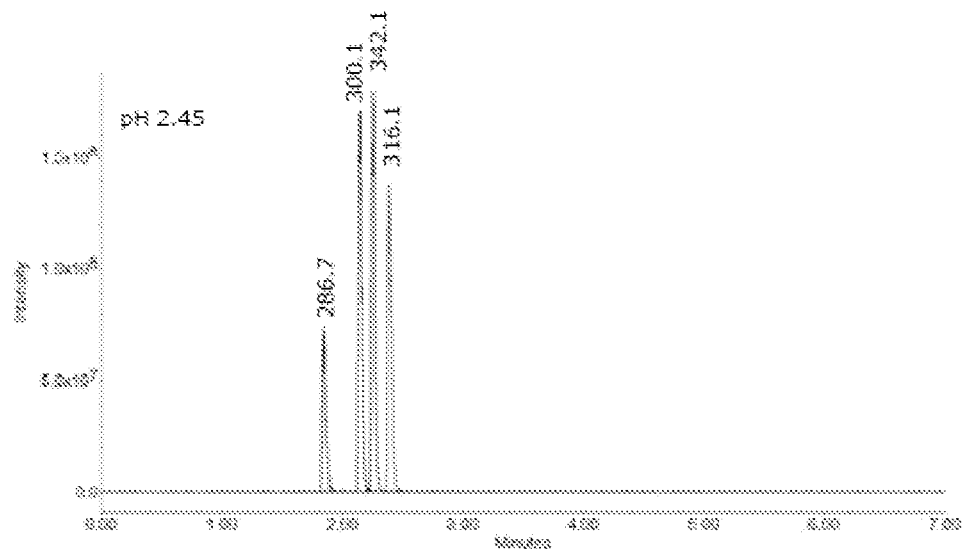
FIG. 3A is a chromatogram showing separation according to the invention as described in the example.
Figure 3B:
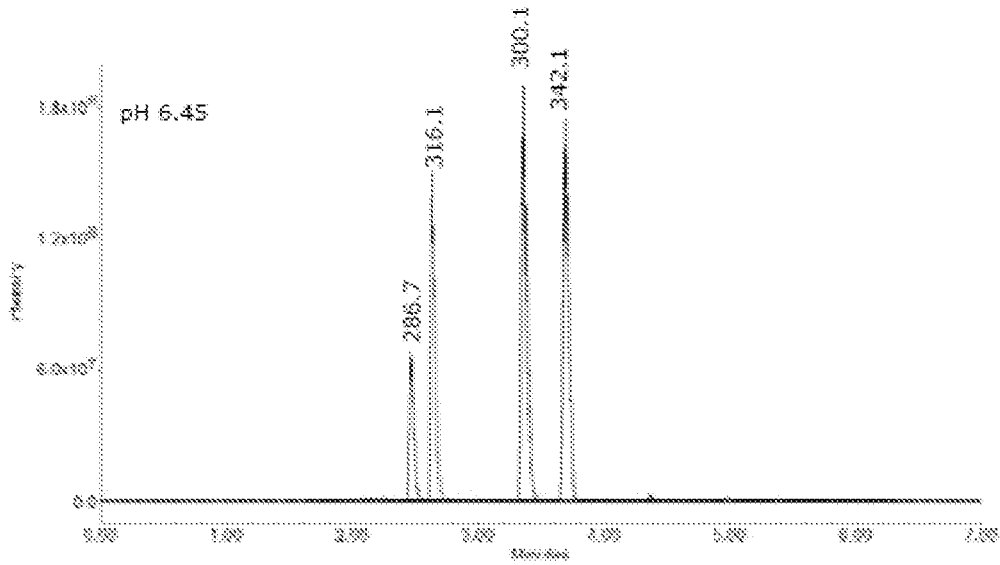
FIG. 3B is a chromatogram showing separation according to the invention as described in the example.
Figure 3C:
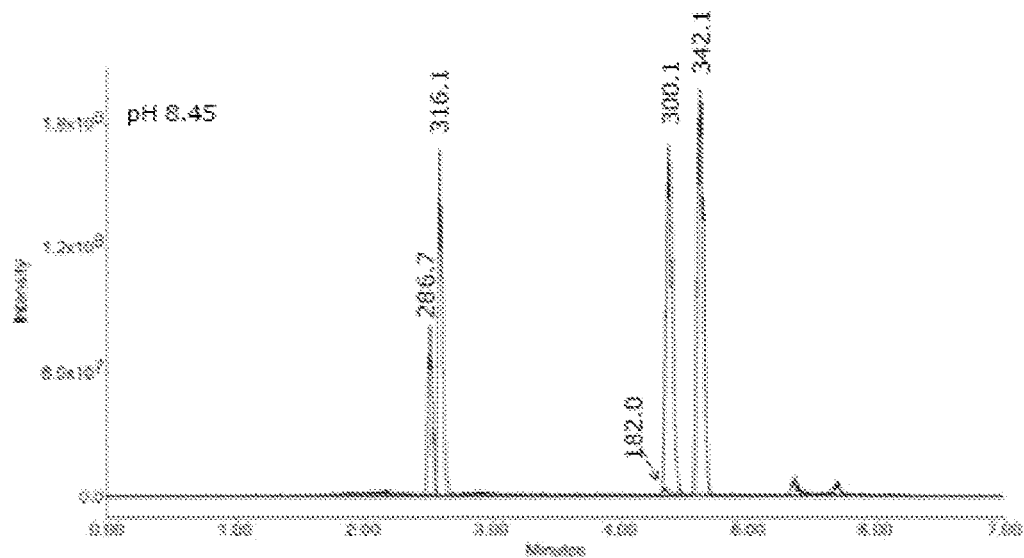
FIG. 3C is a chromatogram showing separation according to the invention as described in the example.
Figure 3D:
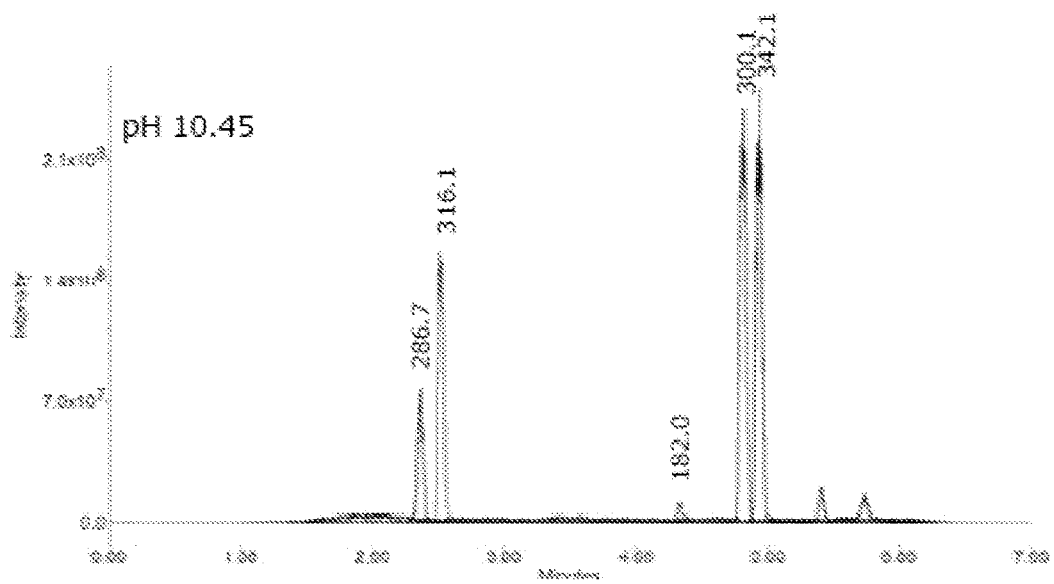
FIG. 3D is a chromatogram showing separation according to the invention as described in the example.

The metoclopramide mixture was analyzed at different points across the range of pH controlled with the system disclosed herein. The separation was monitored with both UV detection and electrospray ionization mass spectrometry (ESI-MS). For example, each peak in the UV chromatogram is labeled with the mass identified by ESI-MS. All chromatographic runs employed the same gradient of increasing methanol (0-60% Methanol over 5 min at 0.6 mL/min at 40° C.). As shown in FIGS. 3A and 3B, the peak with m/z 316.1 is the last peak at pH 2.45 (FIG. 3A), but has moved to elute second at pH 6.45 (FIG. 3B). As shown in FIGS. 3C and 3D, the last two peaks move to later retention as pH is increased. At pH 8.45 (FIG. 3C), a small peak of m/z 182.0 becomes apparent as a coelution with m/z 300.1. At pH 10.45 (FIG. 3D), all 5 peaks are completely resolved.

What is claimed is:

1. A method of preparing a liquid mixture, the mixture comprising an acid solution comprising a volatile acid, a base solution comprising a volatile base, a solvent comprising an organic solvent, and water, the method comprising:

i) calculating with a processor pH and/or solvent concentration at a particular time t from a user-determined gradient function;
ii) based on the values obtained in step (i), calculating with a processor percent acid solution, percent base solution, percent solvent and percent water in the liquid mixture at time t; and
iii) controlling with a machine a liquid mixture preparation device that comprises a mixed liquid outlet port and a plurality of inlet ports connected to component sources of the acid solution, the base solution, the solvent, and the water, wherein relative component proportions are supplied through the inlet ports of the liquid mixture preparation device and are controlled as a function of time t using the percent acid solution, percent base solution, percent solvent and percent water values calculated in ii).

2. The method according to claim 1, wherein the gradient function is based on the following equation:

$$y = y_s + (y_n - y_s) \times \text{fraction} \quad \text{(equation 1)}$$

where y is selected from the group consisting of pH and solvent concentration, $y_s$ is the value at time 1 and $y_n$ is the value at time 2.

3. The method of claim 1, wherein the solvent includes one or more of acetone, acetonitrile, methanol, ethanol, n-propanol and isopropanol, and tetrahydrofuran (THF).

4. The method of claim 1, wherein the acid solution includes one or more of maleic acid, citric acid and succinic acid.

5. The method of claim 1, wherein the base solution includes one or more of 4-methyl morpholine, morpholine, ammonium hydroxide and piperidine.

6. The method of claim 1, wherein a computer program is used for determining relative proportions of acid solution, base solution, solvent and water.

7. The method of claim 1, wherein the solvent includes one or more of acetone, acetonitrile, methanol, ethanol, n-propanol and isopropanol, and tetrahydrofuran (THF), wherein the acid solution includes one or more of maleic acid, citric acid and succinic acid, and wherein the base solution includes one or more of 4-methyl morpholine, morpholine, ammonium hydroxide and piperidine.

8. The method of claim 1, wherein the gradient function comprises a fraction multiplier that provides predetermined changes in pH and/or solvent concentration, each being independent of the other, over a time period of interest.

9. The method according to claim 8, wherein the fraction multiplier is selected from the group consisting of:

$$\text{fraction} = 1.0, \quad 1$$

$$\text{fraction} = 1 - \left(1 - \frac{t}{t_1 - t_0}\right)^8, \quad 2$$

$$\text{fraction} = 1 - \left(1 - \frac{t}{t_1 - t_0}\right)^5, \quad 3$$

$$\text{fraction} = 1 - \left(1 - \frac{t}{t_1 - t_0}\right)^3, \quad 4$$

$$\text{fraction} = 1 - \left(1 - \frac{t}{t_1 - t_0}\right)^2, \quad 5$$

$$\text{fraction} = \frac{t}{t_1 - t_0}, \quad 6$$

$$\text{fraction} = \left(\frac{t}{t_1 - t_0}\right)^2, \quad 7$$

$$\text{fraction} = \left(\frac{t}{t_1 - t_0}\right)^3, \quad 8$$

$$\text{fraction} = \left(\frac{t}{t_1 - t_0}\right)^5, \quad 9$$

$$\text{fraction} = \left(\frac{t}{t_1 - t_0}\right)^8 \text{ and} \quad 10$$

$$\text{fraction} = 0 \text{ if } t < (t_1 - t_0) \text{ and fraction} = 1 \text{ if } t = (t_1 - t_0). \quad 11$$

10. The method according to claim 1, wherein for a particular pH or solvent concentration the % base can be calculated, using interpolation, from values provided in a look-up table.

11. The method according to claim 10, wherein the pH look-up table is empirically derived or is calculated from the $pK_a$ of the acid.

12. The method according to claim 11, wherein the pH look-up table provides pH values for a given acid+base percentage, ratio, or relative concentration.

13. The method according to claim 11, wherein the pH look-up table provides pH values for a given acid+base percentage, ratio, or relative concentration, and solvent concentration.

14. The method according to claim 11, wherein the pH look-up table provides pH values for a given acid+base percentage, ratio, or relative concentration, solvent concentration and temperature.

15. An eluent preparation device comprising
i) a liquid mixture preparation device comprising a mixed liquid outlet port and a plurality of inlet ports connected to component sources comprising an acid solution comprising a volatile acid, a base solution comprising a volatile base, a solvent comprising an organic solvent, and water, and
ii) a mixer control unit arranged to control the relative component proportions supplied through the inlet ports of the liquid mixture preparation device, wherein the mixer control unit is configured to i) calculate pH and solvent concentration as a function of time t from a gradient function; ii) based on the values obtained in step (i), calculate percent acid, percent base, percent solvent, and percent water in the liquid mixture as a function of time t; and iii) control the acid solution, the base solution, the solvent and the water as a function of time t based on values calculated for percent acid solution, percent base solution, percent solvent and percent water in ii).

16. The liquid chromatography system of claim 15 wherein the system comprises a low-pressure mixing system.

17. The liquid chromatography system of claim 15 wherein the system comprises a high-pressure mixing system.

18. The eluent preparation device of claim 15, wherein the solvent includes one or more of acetone, acetonitrile, methanol, ethanol, n-propanol and isopropanol, and tetrahydrofuran (THF), wherein the acid solution includes one or more of maleic acid, citric acid and succinic acid, and wherein the base solution includes one or more of 4-methyl morpholine, morpholine, ammonium hydroxide and piperidine.

19. A liquid chromatography system comprising the eluent preparation device of claim 15.

20. The liquid chromatography system of claim 19, wherein the solvent includes one or more of acetone, acetonitrile, methanol, ethanol, n-propanol and isopropanol, and tetrahydrofuran (THF), wherein the acid solution includes one or more of maleic acid, citric acid and succinic acid, and wherein the base solution includes one or more of 4-methyl morpholine, morpholine, ammonium hydroxide and piperidine.

* * * * *